United States Patent [19]
Lee et al.

[11] Patent Number: 5,990,322
[45] Date of Patent: Nov. 23, 1999

[54] ALPHA-TOCOPHEROL CYCLOPROPYLATES, THE NEW VITAMIN E DERIVATIVES AND METHOD FOR PRODUCING THE SAME

[75] Inventors: Sijoon Lee; Heui-young Cheong, both of Taejon, Rep. of Korea

[73] Assignee: SK Corporation, Seoul, Rep. of Korea

[21] Appl. No.: 09/265,727

[22] Filed: Mar. 9, 1999

[51] Int. Cl.⁶ .................................................. C07D 311/72
[52] U.S. Cl. ............................................................ 549/410
[58] Field of Search ............................................. 549/410

[56] References Cited

U.S. PATENT DOCUMENTS 4,039,559  8/1977  Nakamura ................................. 549/410

*Primary Examiner*—Laura L. Stockton
*Attorney, Agent, or Firm*—Abelman, Frayne & Schwab

[57] ABSTRACT

The present invention relates to novel alpha-tocopherol cyclopropylates, represented by the following formula I:

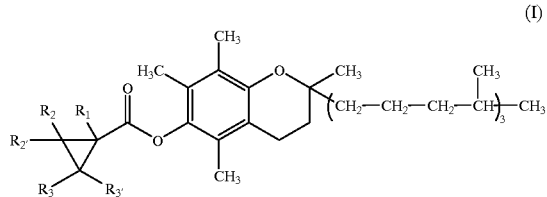

wherein $R_1$, $R_2$, $R_{2'}$, $R_3$ and $R_{3'}$, which may be the same or different, each is a hydrogen atom, a linear or branched $C_1$–$C_{10}$ alkyl chain, phenyl, acetyl or halogen.

11 Claims, 4 Drawing Sheets

ALPHA-TOCOPHEROL CYCLOPROPYLATES, THE NEW VITAMIN E DERIVATIVES AND METHOD FOR PRODUCING THE SAME

FIELD OF THE INVENTION

The present invention relates, in general, to novel alpha-tocopherol cyclopropylates, new vitamin E derivatives and to a method for producing the same and, more particularly, to saturated cyclohydrocarbon carboxy esters of fat-soluble vitamin E, i.e., novel alpha-tocopherol cyclopropylates represented by the following formula I, which comprise cyclohydrocarbon carboxylic acid with a cyclopropyl functional group, and to a method for producing the same:

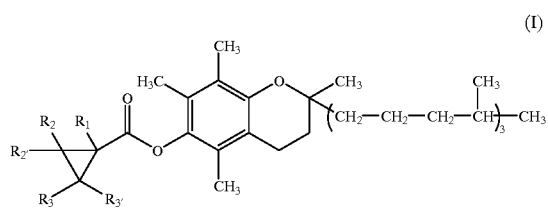

(I)

wherein $R_1$, $R_2$, $R_{2'}$, $R_3$ and $R_{3'}$, which may be the same or different, each is a hydrogen atom, a linear or branched $C_1$–$C_{10}$ alkyl chain, phenyl, acetyl or halogen.

BACKGROUND OF THE INVENTION

Cyclopropane carboxylic acid derivatives are generally represented by the following formula II:

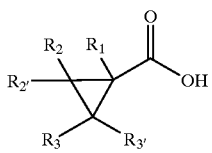

(II)

wherein $R_1$, $R_2$, $R_{2'}$, $R_3$ and $R_{3'}$, which may be the same or different, each is a hydrogen atom, a linear or branched $C_1$–$C_{10}$ alkyl chain, phenyl, acetyl or halogen.

The compounds represented by the formula II have been widely used as a functional group having a specific activity in the compounds recently used in various kinds of medicines and agricultural medicines. Various kinds of derivatives, such as cyclopropane carboxylic acids and ester derivatives thereof, cyclopropane methanol have been widely used in commercialized pyrenoids insecticides and antibiotics, and are very important in medicine/agricultural medicine fields in various forms.

In addition, vitamin E (DL-alpha-tocopherol), represented by the following formula III, is a physiologically essential vitamin among the various vitamins, like vitamin A, C, D, K, beta-carotene and so forth. Vitamin E is relatively complicated in its structure and is widely used as a nutrient, medicines, parturifacient, antioxidant and so forth:

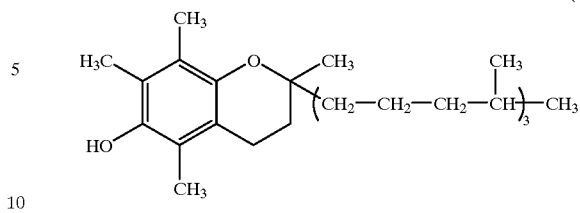

(III)

In spite of its importance, Vitamin E, a compound possessing a benzene ring to which hydroxy group binds, is unstable because it itself is easily oxidized. Tocopherol quinone, an oxidized product of vitamin E, no longer has the biological activity of vitamin E. Thus, because storage and management of vitamin E in itself are difficult, there are many attempts in order to increase stability of vitamin E by converting it to other derivative forms.

Representatives of the above mentioned derivatives are esters, which have an enhanced stability by converting the hydroxyl group in phenol ring, specially weak to oxidize, to an ester form. In the above manner, various tocopherols have been made, and examples of such derivatives include tocopherol acetate, tocopherol succinate, tocopherol phosphate $Na^+$ salt and so on, which are represented by the following formula IV:

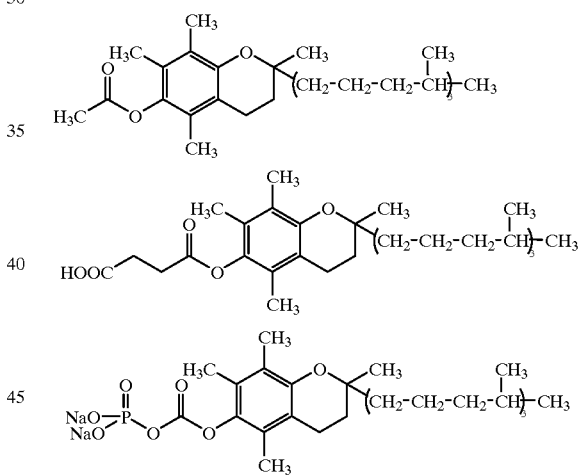

Because these esters have pharmaceutically acceptable stability in addition to being very easy to handle, they are effectively used as replacements for vitamin E.

Upon oral administration, the vitamin E esters are absorbed into the intestinal track and hydrolyzed completely, that is, into free tocopherol and acids by pancreatic enzymes and intestinal enzymes. Thus, the vitamin E esters are absorbed in the form of free tocopherol into the living body. In other words, the esters, when used as replacements for vitamin E in the living body, are converted into free vitamin E and absorbed in the living body, so that the biological effect they have on the living body is practically equivalent to that of vitamin E.

Vitamin E derivatives represented by the following formula V has been filed by the present applicant on Apr. 28, 1997 in Korea under Patent Application No. 97-15961:

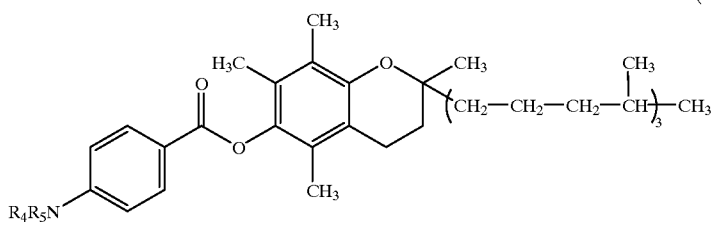

wherein $R_4$ and $R_5$ which may be the same of different, each is a hydrogen atom or a linear or branched $C_1$–$C_4$ alkyl chain.

DETAILED DESCRIPTION

Therefore, it is an object of the present invention to provide novel pharmaceutically active compounds which have the equal biological activity to that of vitamin E but a more beneficial effect on the living body.

It is another object of the present invention to provide a method for producing such a compound.

In accordance with an embodiment of the present invention, there is provided a compound represented by the following formula I:

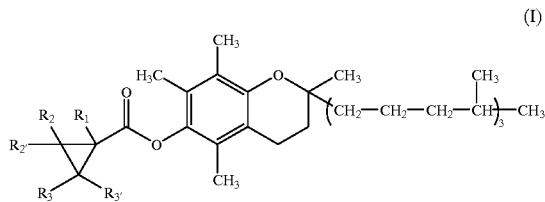

wherein $R_1$, $R_2$, $R_{2'}$, $R_3$ and $R_{3'}$, which may be the same or different, each is a hydrogen atom, a linear or branched $C_1$–$C_{10}$ alkyl chain, phenyl, acetyl or halogen.

In accordance with another embodiment of the present invention, there is provided a method for producing the compound of the formula I, comprising the reacting cyclopropane carboxylic acid halide produced by using the cyclopropane carboxylic acid represented by the following formula II as starting material:

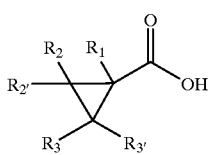

wherein $R_1$, $R_2$, $R_{2'}$, $R_3$ and $R_{3'}$ are as defined above, with alpha-tocopherol represented by the following formula III:

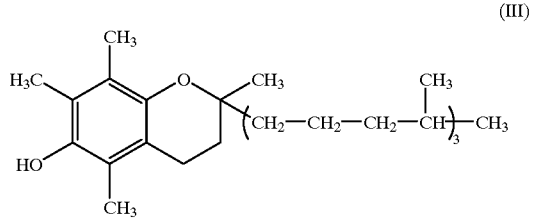

in a solvent and in the presence of a base catalyst.

BEST MODE FOR CARRYING OUT THE INVENTION

Figure 1:
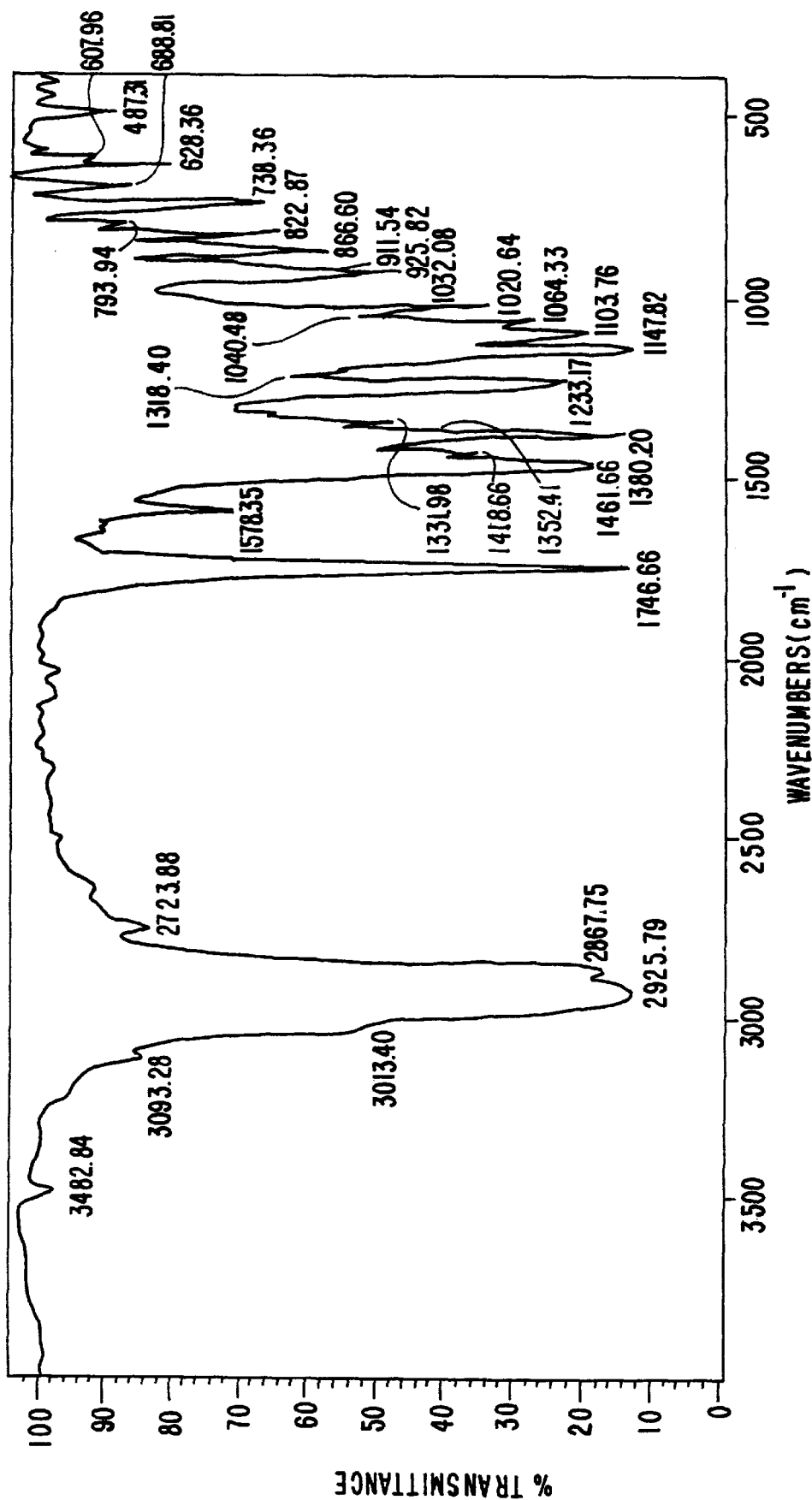
FIG. 1 shows an infrared adsorption spectrum spectroscopy of the compound prepared according to Example I.

The compounds of the formula I, consisting of cyclopropane carboxylic acid and alpha-tocopherol, are a kind of representative esters but, to our knowledge, novel compounds which have not been reported, thus far.

These novel compounds may be prepared by the esterification of alpha-tocopherol with cyclopropane carboxylic acid halide. A useful cyclopropane carboxylic acid halide may result from the reaction of thionyl chloride with cyclopropane carboxylic acid, as shown in the following reaction scheme I:

(Reaction Scheme I)

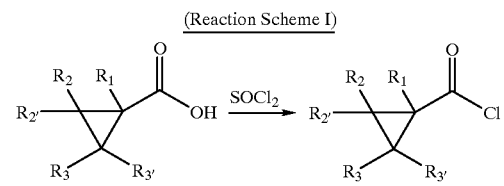

wherein $R_1$, $R_2$, $R_{2'}$, $R_3$ and $R_{3'}$, which may be the same or different, each is a hydrogen atom, a linear or branched $C_1$–$C_{10}$ alkyl chain, phenyl, acetyl or halogen.

The cyclopropane carboxylic acid halide was prepared by using a modification of procedure described in a prior literature. Without using a particular solvent, the reaction was carried out: thionyl chloride was used as a reactant as well as a solvent. After completion of the reaction, un-reacted thionyl chloride and hydrochloric acid, a by-product, were removed by heating and fractional distillation depending upon the kind of cyclopropane carboxylic halides which were prepared, and the residue was distilled in vacuo to obtain cyclopropane carboxylic acid halide.

The preparation of the alpha-tocopherol cyclopropylate represented by the formula I is shown in the following reaction scheme II:

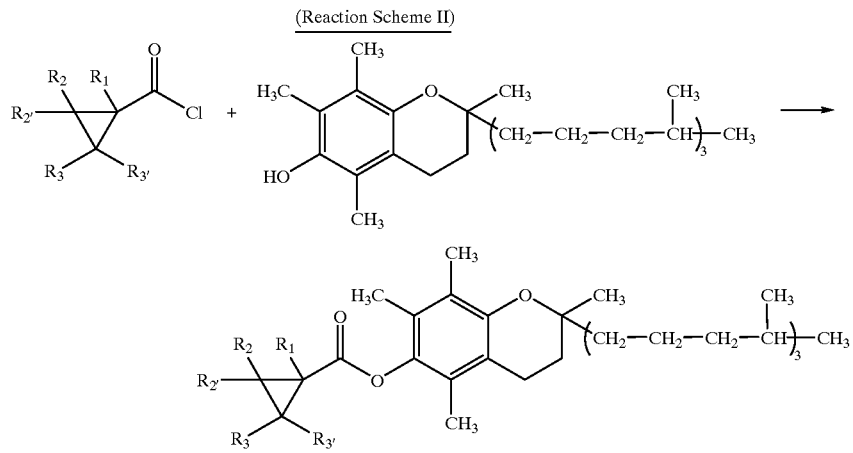

(Reaction Scheme II)

wherein $R_1$, $R_2$, $R_{2'}$, $R_3$ and $R_{3'}$ are as defined above.

This reaction can be effectively carried out in the presence of a base such as tertiary amine in an aprotic solvent or an aromatic hydrocarbon solvent.

Aprotic solvents are selected from the group consisting of acetonitrile, tetrahydrofuran, dichloromethane and so forth. Aromatic hydrocarbon solvents are selected from the group consisting of benzene, toluene and so on, but acetonitrile is preferable in view of reaction rate and yield.

In addition, as for the base, it may be selected from the group consisting of pyridine, pyridine/4-(dimethylamino) pyridine and triethylamine. While the first two show similar reaction rate and yield each other, triethylamine is relatively poorer in reaction rate and yield.

Generally, the ratio of the reactants and the base, for example, the molar ratio of alpha-tocopherol:cyclopropane carboxylic acid halide:base, is in a range of 1.0:1.5–8.0:1.2–5.0 and preferably 1.0:4.0–7.0:1.5–2.5.

This reaction is carried out at a temperature range from 0° C. to the boiling point of the solvent (about 120° C.), and preferably from room temperature to 35° C.

The reaction came to the end at 5 hours after the initiation, and preferably the reaction is carried out for about 4–5 hours.

The objective product may be isolated and purified through solvent extraction from the reaction mixture, tube chromatography and/or recrystallization. Where undissolved products are present in the reaction mixture, they are first removed by filtration, and followed by the purification for the final product through the same techniques.

A better understanding of the present invention may be obtained in light of the following examples which are set forth to illustrate, but are not to be construed to limit, the present invention.

EXAMPLE I

In an 1 L round-bottom flask, alpha-tocopherol (20 g, 46 mM) was dissolved in anhydrous acetonitrile (300 ml) by stirring under a nitrogen atmosphere. Pyridine (8 ml, 103 mM) was added thereto and stirred for 10 min. And then, cyclopropane carbonyl chloride solution (150 ml) which made through dissolving the cyclopropane carbonyl chloride (29.5 ml, 245 mM) in acetonitrile, was added slowly under a nitrogen atmosphere by using a dropping funnel (the molar ratio of each reactant, alpha-tocopherol:cyclopropane carbonyl chloride:pyridine, is 1.0:5.3:2.2).

After completion of the addition for about 1 hour, the mixture was stirred at room temperature. The progress of the reaction was monitored by a thin layer chromatography or gas chromatography. As a result of observation as time, it was found that the reaction completely proceeded after 4 hours since the stirring. Henceforth, the acetonitrile solvent was removed from the reaction mixture by use of rotary evaporator.

The residue was dissolved in diethylether (200 ml) and the solution was moved to a separate funnel. And then, the organic layer was washed with distillation water (200 ml * 1), followed by IN aqueous hydrochloride (150 ml * 2), and followed by distillation water (150 ml * 2) again. The resulting organic layer was dried over magnesium sulfate ($MgSO_4$) and filtered, and the solvent was removed from the organic layer by use of rotary evaporator.

As a result of HPLC, alpha-tocopherol cyclopropylate having 95% purity was obtained, and isolated and purified through tube chromatography on silica gel eluting with hexane/ethyl acetate mixture (10:1, v/v) to afford pure alpha-tocopherol cyclopropylate as a pale yellow oil (20.1 g): Yield 87%.

Figure 2:
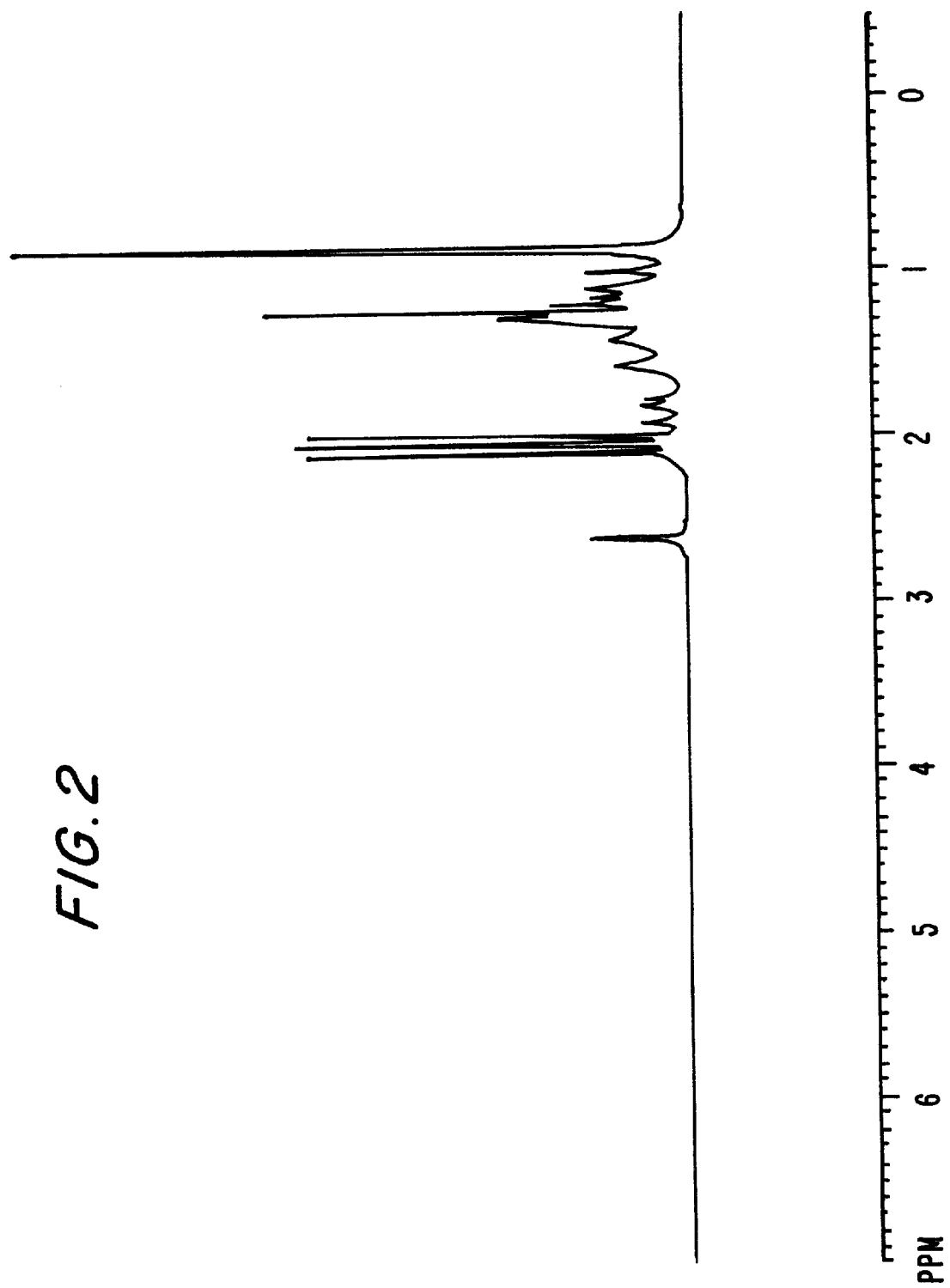
FIG. 2 shows an $^1$H-NMR spectrum of the compound prepared according to Example I.
Figure 3:
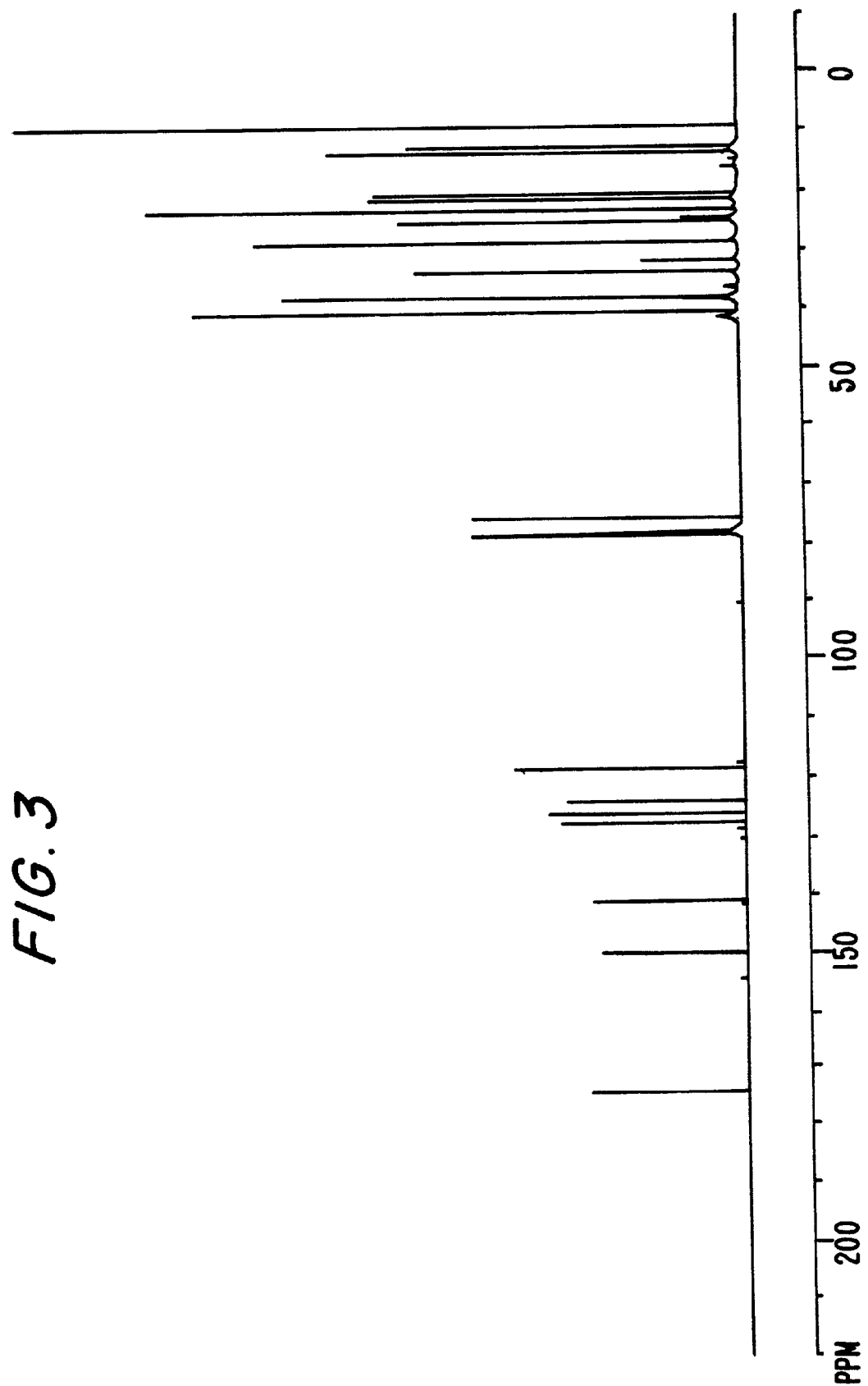
FIG. 3 shows a $^{14}$C-NMR spectrum of the compound prepared according to Example I.
Figure 4:
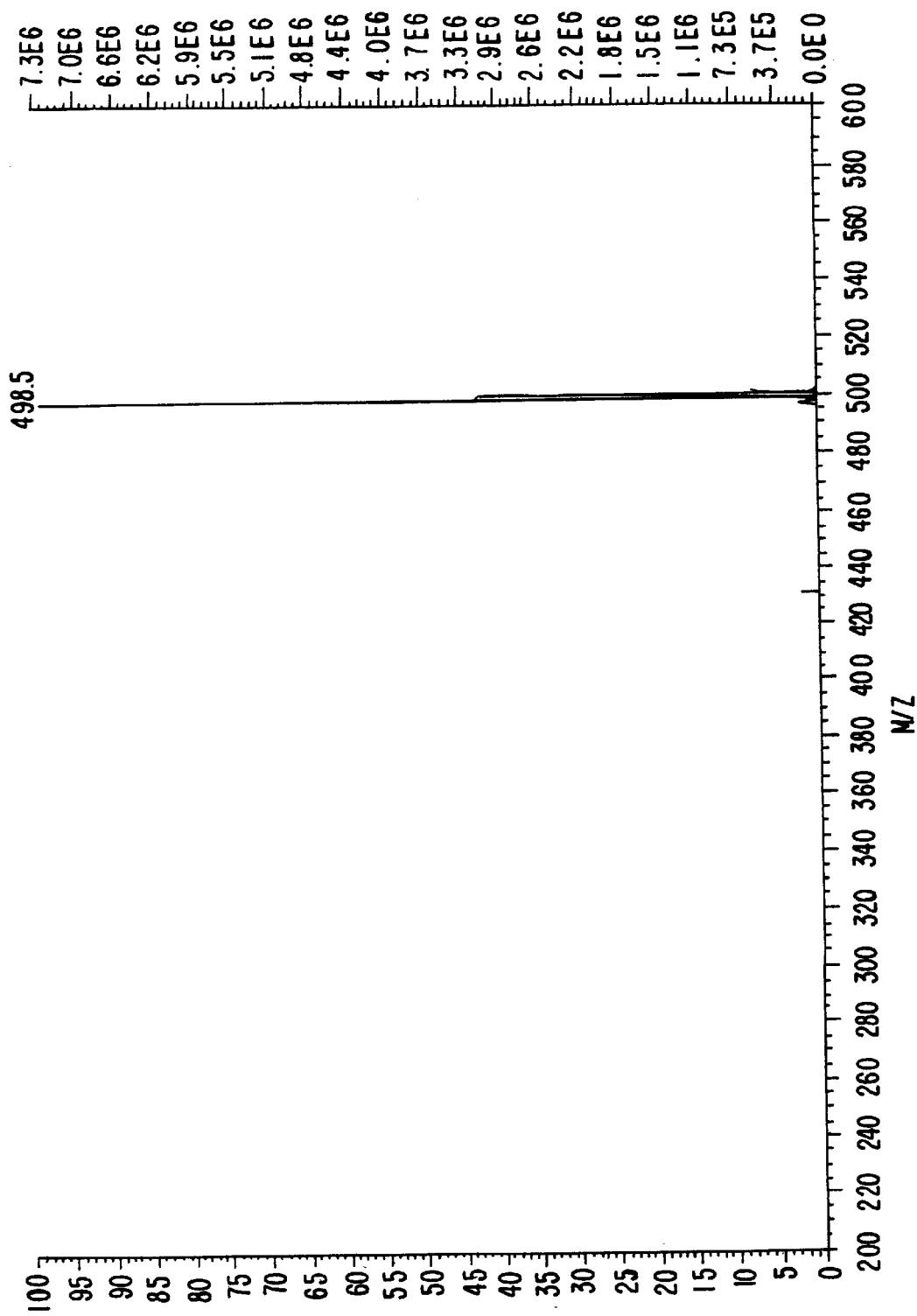
FIG. 4 shows a mass spectrum of the compound prepared according to Example I.

Its structure was identified by infrared spectrometry (FIG. 1), proton nuclear magnetic resonance spectroscopy ($^1$H-NMR, FIG. 2), carbon nuclear magnetic resonance spectroscopy (FIG. 3) and mass spectroscopy (FIG. 4).

EXAMPLE II

The reaction of alpha-tocopherol with cyclopropane carbonyl chloride was carried cut in the presence of pyridine, in the same manner with Example I, except that the amount of alpha-tocopherol, cyclopropane carbonyl chloride and pyridine was 11.6 mM, 23.1 mM and 20.0 mM (the ratio of moles=1.0:2.0:1.7), respectively. This reaction was performed in the same method as that of Example I, to produce pure alpha-tocopherol cyclopropylate (3.47 g, yield 60%).

EXAMPLE III

Alpha-tocopherol cyclopropylate was prepared in the same manner with Example I, except for using dichloromethane, instead of acetonitrile, and that the alpha-tocopherol, the cyclopropane carbonyl chloride and the pyridine are present at a molar ratio of 1.0:5.3:2.2. The reaction was performed at room temperature for 4 hours.

Gas chromatography showed that 76% of the alpha-tocopherol used upon reacting was not reacted. The remaining processes of Example I were repeated to produce alpha-tocopherol cyclopropylate (yield 20%).

EXAMPLE IV

The procedure of Example III was repeated, except for using toluene as solvent. The remaining processes of Example I were repeated to produce alpha-tocopherol cyclopropylate (yield 50%).

EXAMPLE V

The procedure of Example III was repeated, except for using tetrahydrofuran as solvent. The remaining processes of Example I were repeated to produce alpha-tocopherol cyclopropylate (yield 29%).

EXAMPLE VI

The procedure of Example III was repeated, except for using benzene as solvent. The remaining processes of Example I were repeated to produce alpha-tocopherol cyclopropylate (yield 5%)).

EXAMPLE VII

The procedure of Example III was repeated, except for using toluene as solvent. The remaining processes of Example I were repeated to produce alpha-tocopherol cyclopropylate (yield 5.5%).

EXAMPLE VIII

The reaction was carried out in the presence of acetonitrile, in the same manner with Example I, except that the alpha-tocopherol, the cyclopropane carbonyl chloride and the pyridine are present at a molar ratio of 1.0:1.9:2.1. The reaction was performed at room temperature for 4 hours.

Gas chromatography showed that 30% of the alpha-tocopherol used upon reacting was not reacted. The remaining processes of Example I were repeated to produce alpha-tocopherol cyclopropylate (yield 66%).

EXAMPLE IX

The reaction was carried out in the presence of acetonitrile, in the same manner with Example I, except that the alpha-tocopherol, the cyclopropane carbonyl chloride and the pyridine are present at a molar ratio of 1.0:3.8:2.1. The reaction was performed at room temperature for 4 hours.

Gas chromatography showed that 12% of the alpha-tocopherol used upon reacting was not reacted. The remaining processes of Example I were repeated to produce alpha-tocopherol cyclopropylate (yield 83%).

EXAMPLE X

The reaction was carried out in the presence of acetonitrile, in the same manner with Example I, except that the alpha-tocopherol, the cyclopropane carbonyl chloride and the pyridine are present at a molar ratio of 1.0:6.5:2.1. The reaction was performed at room temperature for 4 hours.

Gas chromatography showed that the alpha-tocopherol used upon reacting was completely converted. The remaining processes of Example I were repeated to produce alpha-tocopherol cyclopropylate (yield 95%).

INDUSTRIAL APPLICABILITY

As described hereinbefore, the compounds according to the present invention are a kind of novel vitamin E esters which are prepared by reacting he alpha-tocopherol and cyclopropane carboxylic acid. The alpha-tocopherol, a fat-soluble essential vitamin E is widely used as an antioxidant, nutrient, medicines, parturifacient and so forth, and the cyclopropane carboxylic acid is recently used as functional group having specific activity in living body, and widely used in commercialized pyrenoids insecticide and antibiotics. The compounds according to the present invention have dual function of vitamin E and cyclopropane carboxylic acid and a good stability against an external factors, especially oxidation. Consequently, the compounds of the invention are fat-soluble vitamin E precursors, as mentioned above, novel vitamin E esters to which cyclopropane carboxylic acid is bound, so that one can expect novel biological activity in itself.

Many modifications and variations of the present invention are possible in light of the above teachings. Therefore, it is to be understood that within the scope of the appended claims, the invention may be practiced otherwise than as specifically described.

What is claimed is:

1. An alpha-tocopherol cyclopropylate, represented by the following formula I:

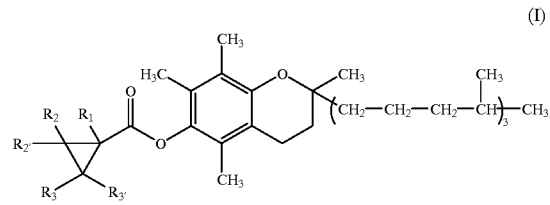

wherein, $R_1$, $R_2$, $R_{2'}$, $R_3$ and $R_{3'}$, which may be the same or different, each is a hydrogen atom, a linear or branched $C_1$–$C_{10}$ alkyl chain, phenyl, acetyl or halogen.

2. The alpha-tocopherol cyclopropylate in accordance with claim 1, wherein $R_1$, $R_2$, $R_{2'}$, $R_3$ and $R_{3'}$ each is a hydrogen atom.

3. The alpha-tocopherol cyclopropylate in accordance with claim 1, wherein $R_1$ is a hydrogen atom and $R_2$, $R_{2'}$, $R_3$ and $R_{3'}$, which may be the same or different, each is a hydrogen atom, a linear or branched $C_1$–$C_{10}$ alkyl chain, phenyl, acetyl or halogen.

4. A method for producing an alpha-tocopherol cyclopropylate represented by the following formula I, comprising reacting cyclopropane carboxylic acid halide produced as shown in the following reaction scheme I, by using cyclopropane carboxylic acid represented by the following formula II as starting material, with an alpha-tocopherol represented by the following formula III in a solvent in the presence of a base:

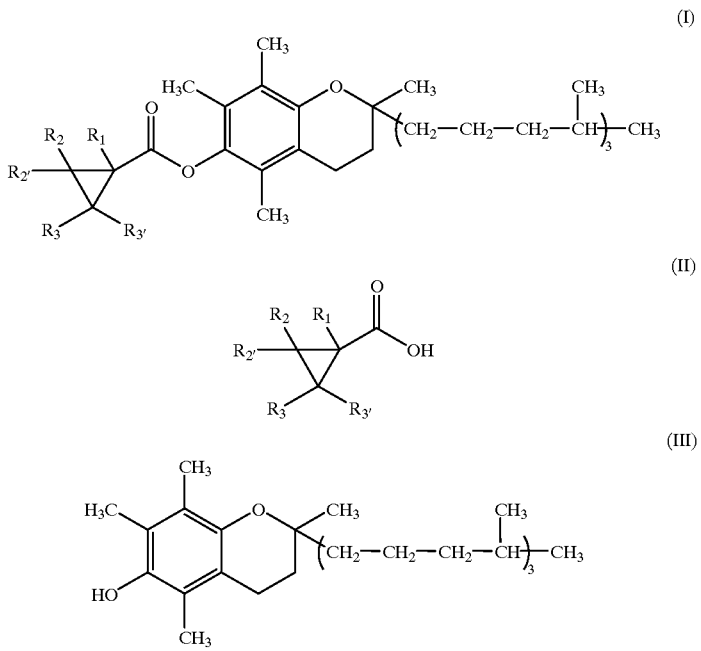

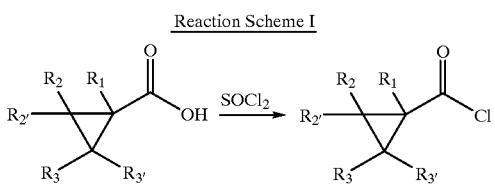

wherein $R_1$, $R_2$, $R_{2'}$, $R_3$ and $R_{3'}$, which may be the same or different, each is a hydrogen atom or a linear or branched $C_1$–$C_{10}$ alkyl chain, phenyl, acetyl or halogen.

5. The method in accordance with claim 4, wherein said solvent is selected from the group consisting of acetonitrile, dichloromethane, tetrahydrofuran, benzene and toluene.

6. The method in accordance with claim 4, wherein said base is selected from the group consisting of pyridine, pyridine/4-(dimethylamino)pyridine and triethylamine.

7. The method in accordance with claim 4, wherein the alpha-tocopherol, the cyclopropane carboxylic acid halide and the base are present at a molar ratio of 1.0:1.5–8.0:1.2–5.0.

8. THe method in accordance with claim 7, the alpha-tocopherol, the cyclopropane carboxylic acid halide and the base are present at a molar ratio of 1.0:4.0–7.0:1.5–2.5.

9. The method in accordance with claim 4, wherein the reaction is carried out at a temperature of 0 to 120° C.

10. THe method in accordance with claim 9, wherein the reaction is carried out at a temperature range from room temperature to 35° C.

11. The method in accordance with claim 4, wherein the reaction is carried out for 4 to 5 hours.

* * * * *